United States Patent
Kraemer et al.

(10) Patent No.: US 7,565,249 B2
(45) Date of Patent: Jul. 21, 2009

(54) METHOD FOR THE DETERMINATION OF A LIGHT TRANSPORT PARAMETER IN A BIOLOGICAL MATRIX

(75) Inventors: Uwe Kraemer, Ilvesheim (DE); Heinz-Michael Hein, Weinheim (DE); Dietmar Volz, Dossenheim (DE)

(73) Assignee: Roche Diagnostics Operations, Inc., Indianapolis (IN)

( * ) Notice: Subject to any disclaimer, the term of this patent is extended or adjusted under 35 U.S.C. 154(b) by 612 days.

(21) Appl. No.: 10/471,113

(22) PCT Filed: Feb. 23, 2002

(86) PCT No.: PCT/EP02/01944

§ 371 (c)(1),
(2), (4) Date: Mar. 12, 2004

(87) PCT Pub. No.: WO02/069790

PCT Pub. Date: Sep. 12, 2002

(65) Prior Publication Data

US 2004/0152089 A1     Aug. 5, 2004

(30) Foreign Application Priority Data

Mar. 6, 2001  (DE) ................... 101 10 599

(51) Int. Cl.
*G06F 19/00*   (2006.01)
*G11C 17/00*   (2006.01)
*G01N 33/66*   (2006.01)

(52) U.S. Cl. ............... 702/19; 365/94; 436/95

(58) Field of Classification Search ........ None
See application file for complete search history.

(56) References Cited

U.S. PATENT DOCUMENTS

| | | | |
|---|---|---|---|
| 5,551,422 A | 9/1996 | Simonsen et al. ........... 128/633 |
| 5,692,504 A * | 12/1997 | Essenpreis et al. ......... 600/316 |
| 5,770,454 A | 6/1998 | Essenpreis et al. ......... 436/164 |
| 5,782,755 A | 7/1998 | Chance et al. |
| 5,825,488 A | 10/1998 | Kohl et al. ................ 356/342 |
| 5,867,807 A | 2/1999 | Yamada et al. ............. 702/30 |
| 6,615,061 B1 * | 9/2003 | Khalil et al. .............. 600/310 |

FOREIGN PATENT DOCUMENTS

EP     0710832 A1    5/1996

OTHER PUBLICATIONS

Bevilacqua, F., et al., "In vivo local determination of tissue optical properties," SPIE, vol. 3194, pp. 262-268.
Farrell, Thomas J., et al., "A diffusion theory model of spatially resolved, steady-state diffuse reflectance for the noninvasive determination of tissue optical properties in vivo," Med. Phys. 19 (4) Jul./Aug. 1992, pp. 879-888.
Haskell, Richard C., et al., "Boundary conditions for the diffusion equation in radiative transfer," J. Opt. Soc. Am. A, vol. 11, No. 10, Oct. 1994, pp. 2727-2741.
Tualle, J.-M., et al., "Real time optical coefficients evaluation from time and space resolved reflectance measurements in biological tissues," Optics Communications 124 (1996) 216-221.
Search report for PCT/EP02/01944, mailed Oct. 29, 2002.
Bruulsema, J.T., Hayward, J.E., Farrell, T.J., and Patterson, M.S., Correlation between blood glucose concentration in diabetics and noninvasively measured tissue optical scattering coefficient, Feb. 1, 2997, Optical Letters, vol. 22, No. 3, pp. 190-192.

* cited by examiner

*Primary Examiner*—John S Brusca
(74) *Attorney, Agent, or Firm*—Baker & Daniels LLP

(57) ABSTRACT

A method is proposed for the selective determination of a light transport parameter which is characteristic for the light scattering in a biological matrix (5), in particular for the purpose of the non-invasive determination of the glucose concentration in the biological matrix. The method comprises providing a plurality of detection measurements, in which light is irradiated as primary light into the biological matrix and measuring an intensity value of secondary light emerging at a plurality of detection sites, located in different measuring distances from the irradiation site. In an evaluation step, the light transport parameter is derived, by means of an evaluation algorithm, from the measured intensity values. For the selective determination of the scattering coefficient, the evaluation algorithm includes a step in which a time derivative value $\Delta_t I(r)$ describing the change of the measurement intensity value versus time is calculated from intensity measurement values obtained at a minimum of two different points of time.

11 Claims, 3 Drawing Sheets

Figure 3:
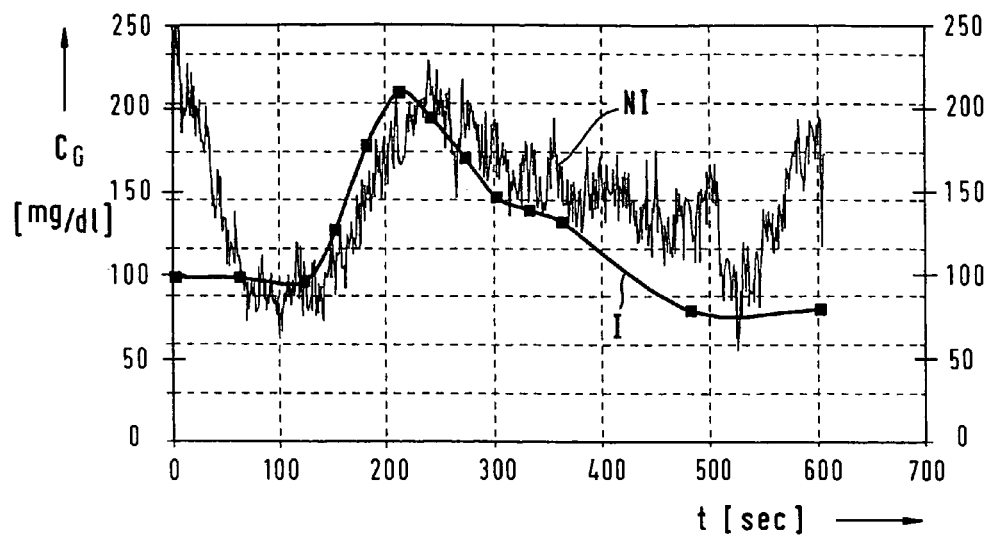

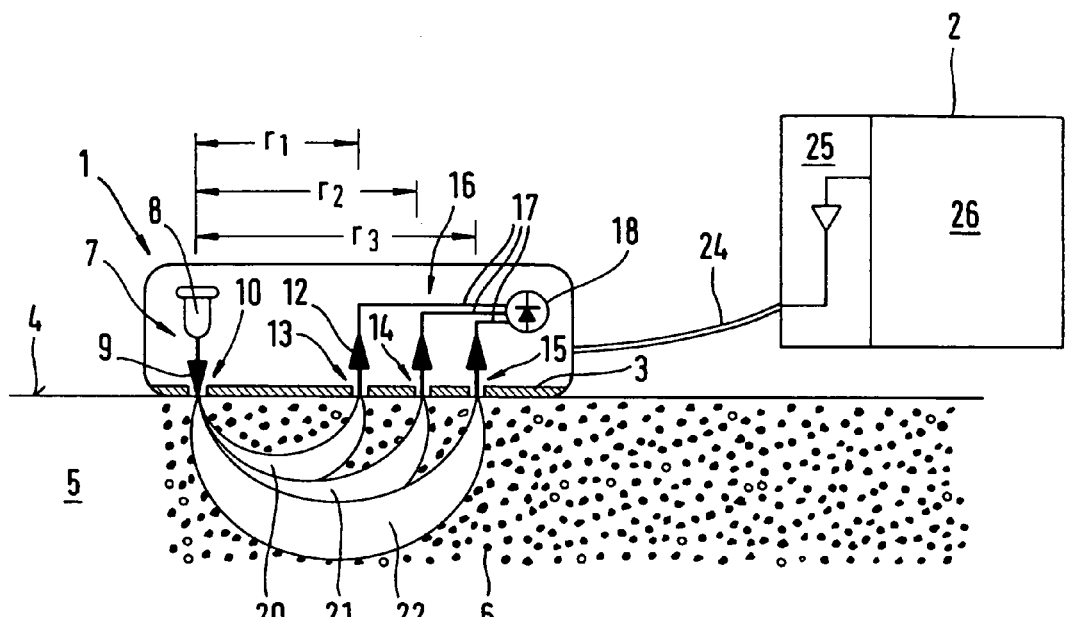
Fig. 1
Fig. 2
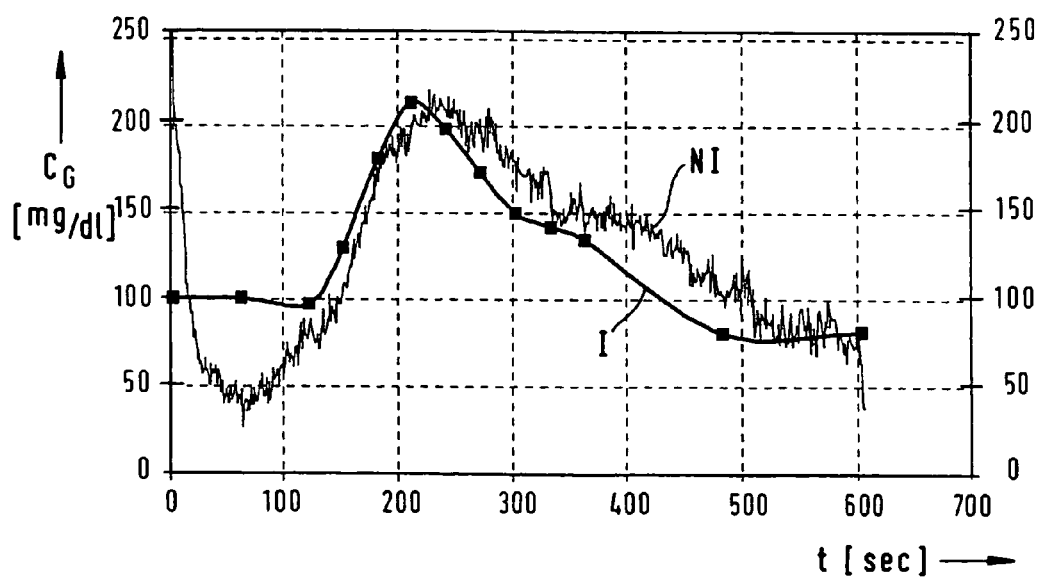

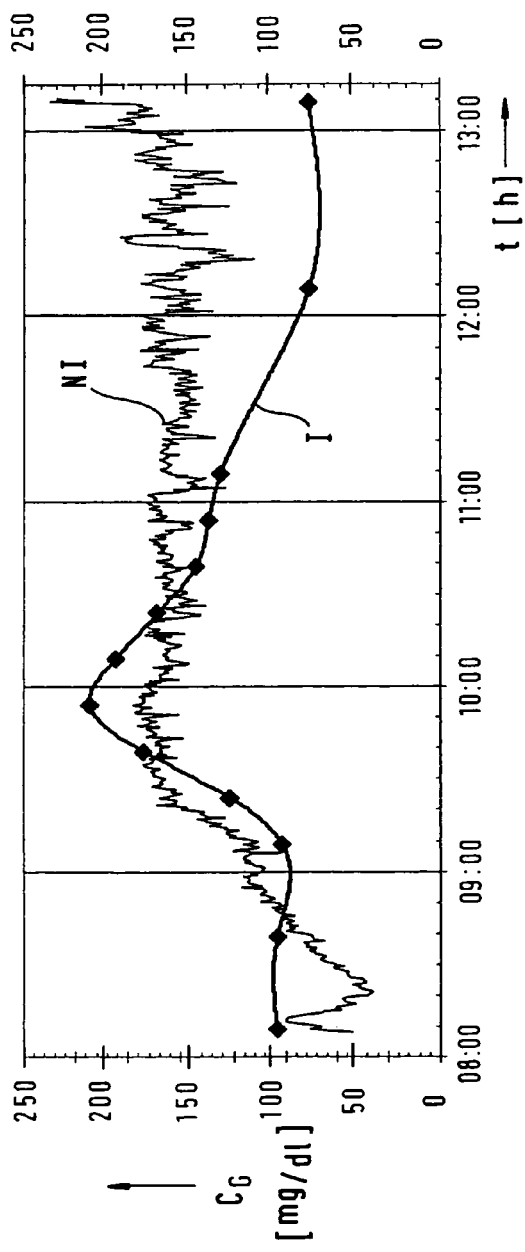
Fig. 5
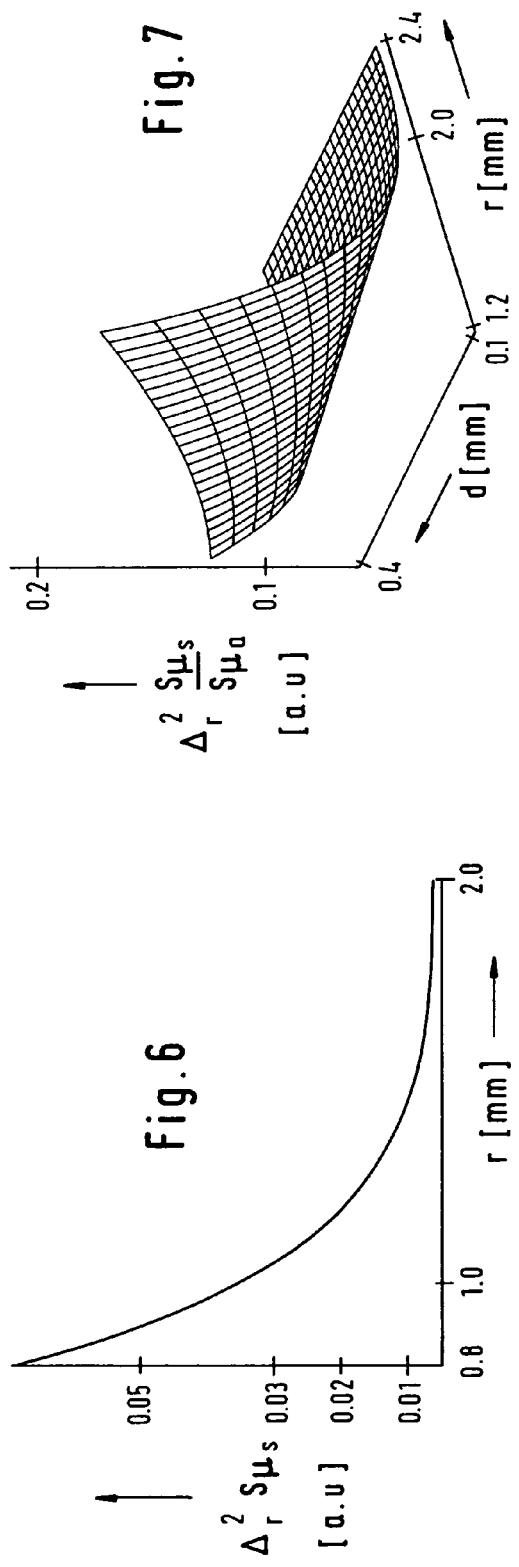
Fig. 7
Fig. 6

METHOD FOR THE DETERMINATION OF A LIGHT TRANSPORT PARAMETER IN A BIOLOGICAL MATRIX

The invention relates to a method for the selective determination of a light transport parameter which is characteristic for the light scattering in a biological matrix, in particular for the purpose of the non-invasive determination of the glucose concentration in the biological matrix.

The term "biological matrix" designates a body liquid or a tissue of a living organism. The biological matrices to which this invention relates are optically heterogeneous, i.e. they contain a plurality of scattering centers, where irradiated light is scattered. In case of a biological tissue, in particular skin tissue, the scattering centers are formed by the cell membranes and other solid components contained in the tissue. Body liquids, in particular blood, are also optically heterogeneous biological matrices containing particles causing multiple scattering of light.

The transport of light in a biological matrix is essentially determined by the light scattering at the scattering centers contained in the matrix and by the optical absorption. Physical quantities quantitatively describing these two properties, are called light transport parameters (scattering parameter or absorption parameter, respectively). The generally used scattering parameter is the scattering coefficient $\mu_s$, and the optical absorption coefficient $\mu_a$ is generally used as absorption parameter. In the scope of this invention it is, however, not necessary to determine these parameters quantitatively in the usual measurement units. Rather the objective of this invention is the reproducible and selective determination of any parameter describing the optical scattering in the biological sample independent from its optical absorption. In the following, the scattering coefficient $\mu_s$ is referred to as a non-limiting example of a scattering parameter.

The selective determination of the scattering coefficient in a biological matrix is of interest for several reasons, for example in the characterization of skin properties in dermatology.

Of particular significance is the investigation of the scattering behavior of a biological matrix for the purpose of non-invasive determination of the glucose concentration. The association between the glucose concentration and the light scattering in biological matrices is described in EP 0659055 B1. As explained therein (as well as in many other publications concerning the analysis of glucose in the human body), the quality of diabetes therapy essentially depends on the determination of the time course of the glucose level in the body with a very high frequency, if possible continuously. This can avoid serious late injuries of diabetes mellitus, for example ablepsia, or serious blood flow disorders, which may lead to the amputation of limbs. The desirable continuous observation of the glucose level is impossible with a conventional invasive method (taking a blood drop from the body of the patient and analyzing it with an analysis system). Therefore, many attempts have been made to determine the glucose concentration noninvasively. More detailed information can be taken from the mentioned European patent.

In the method described in EP 0659055 B1, a plurality of "detection measurements" is performed in order to determine the glucose value; in these, light is radiated as primary light at a defined irradiation site into the biological matrix, the light propagates within the biological matrix along a light path, and an intensity value of the secondary light coming out at a defined detection site is measured. In an evaluation step the glucose concentration is determined from the dependency of the intensity value on the measuring distance between the respective irradiation site and the respective detection site, using an evaluation algorithm and a calibration.

The surprising finding that the course of the glucose concentration in the skin tissue or in another biological matrix can be derived from measurements of this kind is explained in EP 0659055 B1 by the fact that the change of the refraction index of the liquid contained in the matrix, caused by variations of the glucose concentration, can (although it is very small) be used for the determination of the glucose concentration, if the scattering behavior of the light is investigated by the measurement method described there. According to a preferred embodiment described in this document the influences of the absorption and the scattering may be separated by evaluating in the evaluation step the intensity distribution of the secondary light as a function of the distance between the detection site and the irradiation site.

Since some time the scientific literature discusses the determination of $\mu_a$ and $\mu_s$ from the dependence I(r) of the intensity I of the secondary light on the measuring distance r (hereafter designated "intensity profile"). The theoretical basis are the diffusion theory and numerical-statistical methods (Monte Carlo calculations). The theory provides a model for a description of the light propagation behavior in a scattering matrix, by means of a mathematical correlation between the intensity profile I(r) and the model parameters used in the model (in particular the light transport parameters $\mu_a$ and $\mu_s$ and the intensity of the irradiated primary light $I_0$). In principle it is possible to determine the light transport parameters by performing a fit in which the theoretically calculated intensity profile is optimally adapted by variation of the model parameters to experimental results. In this context the following publications can be referred to:

1) T. J. Farrell et al.: "A diffusion theory model of spatially resolved, steady-state diffuse reflectance for the noninvasive determination of tissue optical properties in vivo", Med. Phys. 19, 879 to 888 (1992)

2) R. C. Haskell et al.: "Boundary conditions for the diffusion equation in radiative transfer", J. Opt. Soc. Am A, 11, 2727 to 2741 (1994)

Although the authors report a good correspondence of measured values and theoretical considerations, these methods did not obtain any practical significance (in particular for the determination of the glucose concentration in a biological matrix).

The patent literature describes different methods addressing the problem to determine $\mu_a$ and $\mu_s$ in a biological matrix in order to obtain analytical data for medical purposes, in particular for the determination of the glucose concentration:

3) According to EP 0760091 B1, at least two frequency domain spectroscopic measurements are performed for at least two different measurement light paths, respectively, for which the phase shift of the secondary light, as compared to the primary light, as well as an intensity measurement value (namely, the DC intensity or the AC intensity) are determined. From these at least four measured values, an absorption parameter and/or a scattering parameter are derived. Frequency domain measuring methods use light modulated in the GHz range, thus causing a high expense with respect to measuring technology.

4) EP 0774658 A2 describes a method in which the reflection properties at the matrix surface are varied in order to analyze the scattering properties of a biological matrix. For example, the contact surface of the measuring head used for the measuring method may have different partial sections with different reflectivity. By these means the reflection properties for two measuring distances are varied at least two times. The document states that the at least four measured values can be used to separate absorption and scattering (either basing on the diffusion theory, or empirically-numerically). However, this method is rather expensive, too. Furthermore, it is difficult to obtain the reproducibility of the measured values which is necessary for the analysis of the glucose concentration.

Based on this the problem addressed by the invention is the selective determination of $\mu_s$ (or any other parameter describing the light scattering) in a biological matrix, with a method allowing easy operation, a lower expense for measurement technology and high accuracy.

This object is achieved by a method for the selective determination of a light transport parameter which is characteristic for the light scattering in a biological matrix, in particular for the purpose of the noninvasive determination of the glucose concentration in a biological matrix, compromising a plurality of detection measurements, in which light is irradiated, as primary light, at an irradiation site into the biological matrix, the light propagates along a light path within the biological matrix and an intensity value of secondary light emerging at a detection site is measured, the detection site being located, for the plurality of detection measurements, at different measuring distances from the irradiation site, and an evaluation step in which the light transport parameter is derived, by means of an evaluation algorithm, from the intensity values measured during the plurality of detection measurements, characterized in that the evaluation algorithm includes a step in which a time derivative value $\Delta_t I(r)$ describing the change of the intensity measurement value versus time is calculated from measurement intensity values obtained at a minimum of two different points of time and using the time derivative value $\Delta_t I(r)$ for the determination of the light transport parameter.

Preferably, the measurement of the intensity values is a DC measurement, in which the primary light is irradiated with constant intensity. However, chopped or intensity modulated primary light and frequency selective measuring methods can also be used. In case of very high modulation frequencies (in the GHz range), a frequency modulation leads to a measurement of the AC intensity. Currently, such a method is less preferred due to the increased measuring expense required for very high measuring frequencies.

In the scope of this invention, the intensity of the secondary light does not need to be measured absolutely. Relative measurements with at least two points of time of measurement, from which a time derivative value can be calculated, are sufficient. Therefore, an intensity measurement value according to the invention is a value of a measured quantity in any unit which provides information about the relative change of the intensity of the secondary light. Such an intensity value for a point of time t and a measuring distance r is hereafter designated I(r,t).

Mathematically expressed, the time derivative value (the relative change versus time of the intensity measurement value for a certain measuring distance r) corresponds to the partial derivative of the function I(r,t) with respect to time $$\partial_t I(r) = \partial \ln I(r,t)/\partial t = \partial I(r,t)/[\partial t \cdot I(r)] \quad (1)$$

In practice, the intensity is measured at a minimum of two discrete points of time $t_i$. From this, the time derivative value is calculated as difference quotient according to $$\Delta_t I(r) = \frac{I(r, t_1) - I(r, t_0)}{I(r, t_o)} \quad (2)$$

In its most general form, the invention requires at least two detection measurements at two different points of time $t_i$ for a single measuring distance $r_0$. Preferably, intensity values for a plurality of different measuring distances (intensity profiles) are measured each at at least two points of time.

An important basis of the invention relates to the fact that the function which describes the dependence of the relative change of the intensity measurement value versus time on the light transport parameters $\mu_a$ and $\mu_s$ and the intensity $I_0$ of the primary light, can be expressed as a sum, the sum terms of which are depending, respectively, on only one of the model parameters ($\mu_a$, $\mu_s$, $I_0$). Expressed mathematically:

$$\partial_t I(r) = \sum_{i=1}^{n} S_{P_i}(r) \partial_t P_i \quad (3)$$

wherein $P_i$ designates the model parameters, $\partial_t P_i$ designates the time derivative of these ($\partial_t P_i = \partial P_i/\partial_t$) and $S_{pi}$ designates the sensitivity of the intensity profile I(r) with respect to the parameter $P_i$. The latter is calculated as follows:

$$S_{P_i}(r) = -\frac{\partial_t \ln I(r)}{\partial_t P_i} \quad (4)$$

For practical measurement technology, this mathematical context means that the time derivative value describing the relative change of the intensity profile versus time is an intermediate value which allows—in a very advantageous way—the separation of the influences of the different model parameters, and thus the selective determination of the scattering coefficient. Deviating from the prior art, the time derivative value is not calculated in order to obtain information about the change of the scattering coefficient or the glucose concentration versus time. Rather the time derivative value represents an intermediate value within the algorithm for the determination of the scattering coefficient or the glucose concentration, respectively. It can be used directly, for example in order to eliminate a parameter, the sensitivity course of which—in dependence of the measuring distance—is known. The value calculated on the basis of this time derivative value (e.g. the scattering coefficient, or the glucose concentration, respectively) is assigned to the mean time of the detection measurements used for calculating the time derivative value.

According to a preferred embodiment, the evaluation algorithm includes steps, in which for at least two different measuring distances between the irradiation site and the detection site, detection measurements are performed at a minimum of two points of time. From the (at least four) intensity measurements at least two time derivative values are calculated. From these time derivative values, the spatial derivative with respect to the measuring distance of the time derivative is calculated. The result of these operations is independent from variations of the primary light intensity $I_0$. Therefore, the variations of the light source intensity, causing a "common mode drift" of the signal, are eliminated from the measurement result.

According to another preferred embodiment, the evaluation algorithm includes steps in which detection measurements are performed for at least three different measuring distances between the irradiation site and the detection site, at a minimum of two points of time. From the resulting (at least six) intensity measurement values at least three time derivative values are calculated. From these time derivative values the second spatial derivative of the time derivative value with respect to the measuring distance is calculated. The second spatial derivative corresponds to the curvature of the function $\partial_t I(r)$. The measurement result obtained is essentially independent from the absorption coefficient $\mu_a$. As far as the validity of the Lambert-Beer absorption law can be presumed, this can be easily explained by the fact that the sensitivity $S_{\mu_a}(r)$, calculated according to equation (4), is a linear function of r. The second derivative of a linear function is zero.

The detection measurements used in the algorithm explained above, are preferably performed with unusually short measuring distances. Preferably, the measuring distances of the two or three detection measurements (more generally expressed, of all detection measurements used for the evaluation algorithm) are shorter than the fourfold, particularly shorter than the threefold mean free path (MFP) of the light in the biological matrix. It is particularly advantageous if at least one of the detection measurements is performed with a measuring distance shorter than the mean free path. The mean free path in the uppermost layers of the human skin is about 0.7 mm. Thus all measuring distances used for skin measurements in the scope of this invention are preferably shorter than 3 mm and more preferably shorter than 2 mm. These short measuring distances allow a very compact design of the measuring head. Therefore, the invention is very appropriate for medical diagnostics of tissue, including endoscopic investigations.

Figure 4:
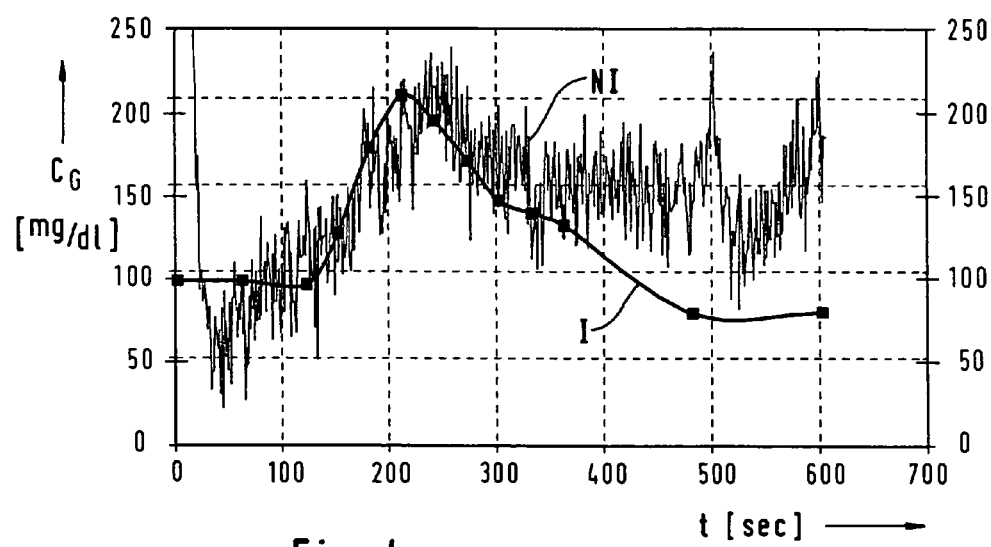

The invention is hereafter described in more detail with respect to the embodiments shown in the figures. The features described can be used individually or in combination in order to create preferred embodiments of the invention:

FIG. 1 shows a schematic sectional view of a device for the optical analysis of a biological matrix, FIG. 2 shows a first plot of a glucose concentration course measured according to the invention in the body of a proband, compared to conventional invasively obtained measurement results, FIG. 3 shows a plot according to FIG. 2, but with different measuring distances, FIG. 4 shows a plot according to FIG. 2, but with another set of different measuring distances, FIG. 5 shows a plot similar to FIG. 2, by which a conventional invasively measured course of the glucose concentration is compared to the measurement results of a prior art non-invasive method basing on the diffusion theory, FIG. 6 shows a plot of the dependence of the scattering sensitivity $S_{\mu_s}$ from the measuring distance, FIG. 7 shows a three-dimensional plot of the dependence of the ratio of the scattering sensitivity $S_{\mu_s}$ to the absorption sensitivity $S_{\mu_a}$ on the measuring distance r and the distance d between the detection sites.

The device for the selective determination of $\mu_s$ in a biological matrix which is shown in highly schematized manner in FIG. 1 essentially consists of a measuring head 1 and a signal processing and evaluation unit 2.

The bottom of a sample contact plate 3 of the measuring head 1 is in contact to a surface 4 of the biological matrix 5 to be investigated which contains a plurality of scattering centers 6. Light irradiation means 7 are located inside the measuring head 1, in the shown case formed by a light emitting diode 8 which irradiates primary light (arrow 9) into the biological matrix 5. The irradiation site 10 of the primary light is defined by a corresponding recess in the skin contact plate 3.

The secondary light, symbolized by the arrows 12 emerging at three detection sites 13, 14 and 15, which are also defined by corresponding recesses of the sample contact plate 3, is detected by a plurality of detection means, together designated as 16. In the embodiment shown the detection means 16 include optical fibers 17, guiding the secondary light of all three detection sites to a common photodetector 18 (for example a photodiode, in particular an avalanche photodiode). In order to enable the necessary separation of the intensity measurement values of the three detection sites, the optical fibers 17 include optical switches (not shown).

The light paths along which the light irradiated into the biological matrix 5 propagates between the irradiation site 11 and the detection sites 12 to 14, are shown symbolically in FIG. 1 and designated 20 to 22. Due to the scattering in the biological matrix, it is of course impossible to identify sharply defined light paths. It can, however, be assumed that the plurality of the photons which are detected as secondary light approximately propagate on a curved light path—similarly as shown in the figure—, the mean penetration depth increasing with the length of the measuring distance r between the irradiation site 10 and the detection sites 12 to 14.

The output signal of the photodetector is led via a cable 24 to an electronic processing system 25 by which it is amplified, processed and digitized in usual manner, so that at its output intensity measurement values are available in digital form which correspond to the intensity of the secondary light emerging at the detection sites 13 to 15.

So far, the shown device is conventional and does not require further explanation. The irradiation means, as well as the detection means, can be light emitters or light sensitive elements are directly integrated into the sample contact plate 3, or may include fiber optics guiding the light from a remote light emitter to the skin contact plate 3, or from there to a remote light receiver. The different measuring distances can be realized by different combinations of irradiation and detection sites. For example, the three measuring distances $r_1$, $r_2$ and $r_3$, shown in FIG. 1, can alternatively be realized by irradiation at three different irradiation sites and measurement at one detection site. Further details about the design of the measuring head, about the detection measurements and about means for measuring intensity values for different measuring distances, can be taken from the published prior art. In particular reference can be made to EP 0659055 B1 which describes different arrangements and designs of the light irradiation means and detection means. The content of this publication is incorporated herein by reference.

The measuring head 1 and the electronic signal processing system 25 are designed such that the electronic signal processing system 25 determines intensity values at any desired point of time and for the measuring distances possible in the respective measuring head (in the shown case the measuring distances $r_1$, $r_2$ and $r_3$), and transmits them in digital form to the electronic evaluation system 26. As explained above, a time derivative value is calculated from at least two intensity values measured at a minimum of two different points of time (equation 2). The time derivative value is used for the determination of the light transport parameter. The calculations are performed by means of a commercial digital computer.

In the experimental evaluation of the invention, the subsequently described experiment was performed with a device essentially designed according to FIG. 1.

A healthy male proband was orally given a glucose drink which effected an increase of his blood glucose value by 130 mg/dl (from 80 mg/dl to 210 mg/dl). Thereafter the glucose value returned to the normal value of 80 mg/dl. A measuring head with an irradiation site in form of a circular point, diameter 0.1 mm) and six detection sites (each having the shape of a circle segment with an aperture angle of 30°) was fixed to the abdomen of this proband. The skin contact surface of the measuring head—and therefore the skin, too—was thermostated to a temperature of 33.5° C. The possible distances between the irradiation site and the detection sites in the measuring head were 0.8 mm, 1.2 mm, 1.6 mm, 2.0 mm, 2.4 mm and 2.8 mm. The primary light was irradiated with a wavelength of 805 nm. The evaluation of the intensity measurement values I(r,t) was performed with the following algorithm:

First, for three measuring distances r, respective time derivative values $\Delta_t i(r)$ were calculated according to equation (2). From these time derivative values the second spatial derivative of the time derivative value with respect to the measuring distance was calculated according to:

$$\Delta_r^2(\Delta_t I(r)) = \Delta_t I(r_1) - 2\Delta_t I(r_2) + \Delta_t I(r_3) \quad (5)$$

This relatively simple formula is true for the preferred special case that the measuring distances $r_1$, $r_2$ and $r_3$ differ in the at least three respective detection measurements by the same value. For arbitrary measuring distances $r_1$, $r_2$ and $r_3$ the following equation can be used:

$$\Delta_r^2(\Delta_t I(r)) = \Delta_t I(r_1) - \Delta_t I(r_2) - \frac{\Delta_t I(r_1) - \Delta_t I(r_2)}{\Delta_t I(r_2) - \Delta_t I(r_3)} \cdot (\Delta_t I(r_2) - \Delta_t I(r_3)) \quad (6)$$

This algorithm was performed with three different measuring distance triples, namely a) $r_1$=0.8 mm, $r_2$=1.2 mm, $r_3$=1.6 mm
b) $r_1$=1.2 mm, $r_2$=1.6 mm, $r_3$=2.0 mm
c) $r_1$=1.6 mm, $r_2$=2.0 mm, $r_3$=2.4 mm The results are shown as measuring curves NI in FIGS. 2 to 4, namely in FIG. 2 for measuring distance triple a, in FIG. 3 for measuring distance triple b and in FIG. 4 for measuring distance triple c. The curves NI designate the respective results of the evaluation algorithm. The bolder curve I shows a comparison measurement, in which the concentration $C_G$ of glucose in the blood was determined invasively. Both curves were normalized at one point. This corresponds to a calibration of the noninvasively measured glucose concentration curve NI by a single invasive control measurement.

The results show:
The course of the measuring curves taken invasively and noninvasively match very well. This proves that the algorithm according to the invention, in which the relative change of the measured intensity profile versus time (not, as according to the prior art, the measured intensity profiles themselves) is used as a basis of the evaluation, allows a very good and easy noninvasive control of the course of the blood glucose level over time.
The shorter the measuring distances used in the corresponding algorithm are, the better are the results.

FIG. 5 shows the results of a comparison experiment in which the same intensity values were evaluated with an algorithm of the prior art. For this purpose, the measured intensity profile (using all measuring distances between 0.8 mm and 2.4 mm) was fitted to a model calculated with the diffusion theory. Again, the result of the noninvasive measurement is designated with NI and a normalization to the conventionally taken measuring curve 1—also included in the graph—was performed at one point. Evidently no acceptable correlation of the calculated results of the noninvasive measurement to the real glucose variation is achieved.

As explained, the best results are obtained using very short measuring distances. In this respect, the invention is fundamentally different from prior methods based on diffusion theory in which—as according to the documents 1) and 2) referred to above—relatively large measuring distances are used. This is also confirmed by the publication 5) F. Bevilacqua et al. "In vivo local determination of tissue optical properties", SPIE Vol. 3194, 262 to 268

The method described therein is to be applied in the optical biopsy used for the detection of malign tissue structures. Therefore a high local resolution is required and a measuring probe with short measuring distances (less than 2 mm) is used. This method, however, requires an absolute measurement and the use of theoretical assumptions with respect to the scattering coefficient (calculated according to the Mie theory). Therefore, it cannot be compared to the method of the present invention.

In order to obtain a better understanding of their experimental results, the inventors calculated, based on the diffusion theory, scattering sensitivities $S_{\mu_s}$ according to equation (4). For equidistant measuring distances with a distance of 0.4 mm between the detection sites, the resulting dependence of the second spatial derivative of the scattering sensitivity $\Delta_r^2 S_{\mu_s}$ (ordinate in arbitrary units) as a function of the measuring distance (r in mm) is shown in FIG. 6. With increasing measuring distance, an approximately exponential decrease of the scattering sensitivity is observed. This confirms that the selectivity of the measurement of the scattering is best with short measuring distances.

FIG. 7 shows, for the case of equidistant measuring distances, the second spatial derivative of the ratio of the scattering sensitivity $S_{\mu_s}$ to the absorption sensitivity $S_{\mu_a}$ as a function of the measuring distance r and the distance d between the detection sites in mm. This graph shows that the ratio between $S_{\mu_s}$ and $S_{\mu_a}$ increases for small measuring distances. This again confirms the results obtained in the experiments.

What is claimed is:

1. A method for selective determination of a light transport parameter which is characteristic for the light scattering in a biological matrix, for the purpose of the non-invasive determination of the glucose concentration in the biological matrix, the method comprising:

performing a plurality of detection measurements, each of said detection measurements comprising:
irradiating light at an irradiation site into the biological matrix;
propagating light inside the biological matrix along a light path;
determining an intensity measurement value of light emerging at a detection site wherein
in at least two of the detection measurements the detection site is located at different measuring distances from the irradiation site;
at least two detection measurements are performed at at least two different points of time for each of said different measuring distances; and
the light transport parameter and the glucose concentration being derived from the intensity measurement values measured by the plurality of detection measurements by means of an evaluation algorithm, and an indication of the glucose concentration is output in a user readable format, said evaluation algorithm comprising:

calculating from the intensity measurement values determined at at least two different points of time for the same measurement distance a time derivative value $\Delta_t I(r)$ as an intermediate value describing the change of intensity versus time for said measurement distance;

calculating at least two intermediate values $\Delta_t I(r)$ for said at least two different measurement distances between irradiation site and detection site; and calculating a spatial derivative with respect to the measurement distance from said at least two intermediate time derivative values $\Delta_t I(r)$.

2. The method according to claim 1, wherein each of the at least two measuring distances is shorter than a fourfold mean free path of the light in the biological matrix.

3. The method according to claim 1, wherein the evaluation algorithm includes determining intensity measurement values of light at detection sites which are located at at least three different measuring distances from the irradiation site at at least two points of time;

calculating time derivative values for each of said at least six different intensity measurement values; and calculating a second spatial derivative of the time derivative values with respect to the measurement distance.

4. The method according to claim 3, wherein each of the at least three measuring distances is shorter than a fourfold mean free path of the light in the biological matrix.

5. The method according to claim 4, where the detection sites are spaced equally apart from each other such that each distance between adjacent detection sites is a constant value.

6. The method according to claim 2, wherein at least one of the measuring distances is shorter than a mean free path of the light in the biological matrix.

7. The method of claim 1, wherein the evaluation algorithm is computer-implemented.

8. A Device for the optical analysis of a glucose concentration in a biological matrix, the device comprising:

a measuring head configured to perform a plurality of detection measurements in which light is irradiated as primary light at an irradiation site into the biological matrix, the light propagate inside the biological matrix along a light path and an intensity measurement value of light emerging as secondary light at a detection site which in the plurality of detection measurements is located at different measuring distances form the irradiation site is measure; and an evaluation unit configured to execute an evaluation algorithm for deriving the light transport parameter from the intensity values measured by the plurality of detection measurements, the evaluation unit outputting an indication of the glucose concentration in a user readable format;

wherein the evaluation algorithm includes steps in which for at least two different measuring distances between irradiation site and detection site a time derivative value $\Delta_t I(r)$ describing the change of the intensity measurement value versus time, is calculated from intensity measurement values obtained at a minimum of two different points of time, and the spatial derivative of the time derivative value with respect to the measuring distance is calculated therefrom.

9. The method of claim 1, wherein each of the at least two measuring distances is shorter than a threefold mean free path of the light in the biological matrix.

10. The method of claim 3, wherein each of the at least three measuring distances is shorter than a threefold mean free path of the light in the biological matrix.

11. A computer readable storage medium comprising a computer program comprising software, wherein the computer program is adapted to be loaded into a computer for executing one or more of the steps of the method of claim 1.

* * * * *